(12) United States Patent
Chang et al.

(10) Patent No.: US 10,667,685 B2
(45) Date of Patent: Jun. 2, 2020

(54) COLLAPSIBLE SURGICAL MIRROR FOR INTRAOCULAR VISUALIZATION

(71) Applicant: Novartis AG, Basel (CH)

(72) Inventors: Grace C. Chang, Lake Forest, CA (US); Nicholas Max Gunn, Newport Beach, CA (US)

(73) Assignee: Alcon Inc. (CH)

( * ) Notice: Subject to any disclaimer, the term of this patent is extended or adjusted under 35 U.S.C. 154(b) by 34 days.

(21) Appl. No.: 15/833,196

(22) Filed: Dec. 6, 2017

(65) Prior Publication Data

US 2018/0160900 A1 Jun. 14, 2018

Related U.S. Application Data

(60) Provisional application No. 62/434,029, filed on Dec. 14, 2016.

(51) Int. Cl.
*A61B 3/117* (2006.01)
*G02B 7/182* (2006.01)
*A61B 3/00* (2006.01)

(52) U.S. Cl.
CPC ............ *A61B 3/117* (2013.01); *A61B 3/0008* (2013.01); *G02B 7/182* (2013.01); *A61B 3/0091* (2013.01)

(58) Field of Classification Search
CPC ...... A61B 3/117; A61B 3/0091; A61B 3/0008
See application file for complete search history.

*Primary Examiner* — Jack Dinh
(74) *Attorney, Agent, or Firm* — Joseph Weatherbee, Esq.

(57) ABSTRACT

The present disclosure provides a small gauge extendable-retractable mirror for use in intraocular surgery. The mirror of the present disclosure can be used in intraocular surgery to enable visualization of areas of the eye currently difficult or impossible to view, such as, e.g., behind the iris.

17 Claims, 6 Drawing Sheets

COLLAPSIBLE SURGICAL MIRROR FOR INTRAOCULAR VISUALIZATION

This application claims the benefit of priority of U.S. Provisional Patent Application Ser. No. 62/434,029 titled "Collapsible Surgical Mirror for Intraocular Visualization", filed on Dec. 14, 2016, whose inventors are Grace Chang and Nicholas Max Gunn, which is hereby incorporated by reference in its entirety as though fully and completely set forth herein.

BACKGROUND

In the following discussion, certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Improved visualization is an unmet need in vitroretinal surgery. Vitroretinal eye surgery includes a group of procedures performed using lasers or conventional surgical instruments deep inside the eye's interior. As the name implies, this delicate surgery takes place in the area of the eye where the gel-like vitreous and retina are found. Various vitreoretinal surgical and laser approaches can restore, preserve, and enhance vision for many eye conditions such as, e.g., diabetic retinopathy, vitreous hemorrhage, macular hole, detached retina, and epiretinal membrane. However, in performing these operations, surgeons have difficulty in viewing, e.g., the periphery of the posterior ocular chamber, and may have to use scleral indentation in order to do so. Additionally, it may be useful to a surgeon to be able to view the area behind the iris and other structures of the eye from the inside of the eye.

Improved visualization may also aid other types of surgery (for example, cataract surgery or other types of surgery in which instruments are being inserted into/removed from the body through a small incision that makes visualization difficult). As another example, it may be helpful for the surgeon to visualize anterior structures in the eye (e.g., the angle of the eye), which may not be possible without specialized lenses.

There is accordingly a need for a surgical instrument that facilitates visualization of the interior areas (e.g., of the eye) currently difficult or impossible to view with current techniques. The present disclosure addresses this need.

SUMMARY

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description, including those aspects illustrated in the accompanying drawings and defined in the appended claims.

One embodiment of the present disclosure provides a small-gauge extendable-retractable mirror for use in ocular surgery. The extendable-retractable mirror of the present disclosure can be used in intraocular surgery to enable visualization of areas of the eye currently difficult or impossible to view, e.g., behind the iris.

Thus, in one embodiment, the present disclosure provides a small gauge extendable-retractable mirror for use in intraocular surgery comprising a body having a proximal end and a distal end, the body defining a first actuation rod passageway and comprising a switch actuator that extends and retracts an actuation rod. The extendable-retractable mirror further includes a 16-30 gauge cannula coupled to and extending from the distal end of the body, the cannula defining a second actuation rod passageway that is coupled to and aligned with the first actuation rod passageway of the body. In some embodiments, the actuation rod may be slidably disposed within the first actuation rod passageway of the body and the second actuation passageway of the cannula. The actuation rod may further be coupled on the proximal end to the switch actuator of the body and coupled on the distal end to a mirror. In some embodiments, the mirror may be capable of retraction within the cannula and extension from the distal end of the actuation rod through the distal end of the cannula. The mirror may include two opposing surfaces with an x dimension in a range of approximately 1.2-6.5 mm (millimeters) and a y dimension in a range of approximately 1.2-6.5 mm. As another example, the mirror may have an x dimension in a range of approximately 2.1-6.5 mm and a y dimension in a range of approximately 2.1-6.5 mm In a more specific example, the mirror may have an x dimension in a range of approximately 2.0-5.5 mm, and more specifically, in a range of approximately 2.5-5.0 mm. Also, in a more specific example, the mirror may have a y dimension in a range of approximately 2.0-5.5 mm, and more specifically, in a range of approximately 2.5-5.0 mm.

In some embodiments, the mirror may be made of nitinol. As another example, the mirror may be made of a reflective material metalized plastic film. In some embodiments, a first opposing surface of the mirror may include a reflective surface that is formed by polishing the first opposing surface of the extendable-retractable mirror. In some embodiments, the first opposing surface of the mirror may be a reflective surface that is formed by depositing a thin layer of reflective material on the first opposing surface of the mirror. In some embodiments, both opposing surfaces of the mirror are reflective.

In some embodiments, the switch actuator that extends and retracts the actuation rod is a sliding switch actuator. Moreover, some embodiments comprise an integrated nanofiber to provide illumination to the mirror. In some embodiments, the integrated nanofiber is coaxial to the actuation rod.

In some embodiments, the small gauge extendable-retractable mirror may include opposing surfaces of the mirror that are flat. In some embodiments, the small gauge extendable-retractable mirror has opposing surfaces of the mirror that are curved (e.g., to provide magnification and/or a wider view).

Some embodiments provide a method for viewing the interior structures of an eye from within the eye comprising inserting the small gauge extendable-retractable mirror into the eye with the mirror in a retracted position; extending the mirror from the cannula by engaging the switch actuator; and viewing the interior structures from the inside of the eye. An additional aspect of this method comprises, after the viewing step, retracting the mirror back into the cannula by engaging the switch actuator.

These and other aspects and uses will be described in the detailed description.

Figure 1A:
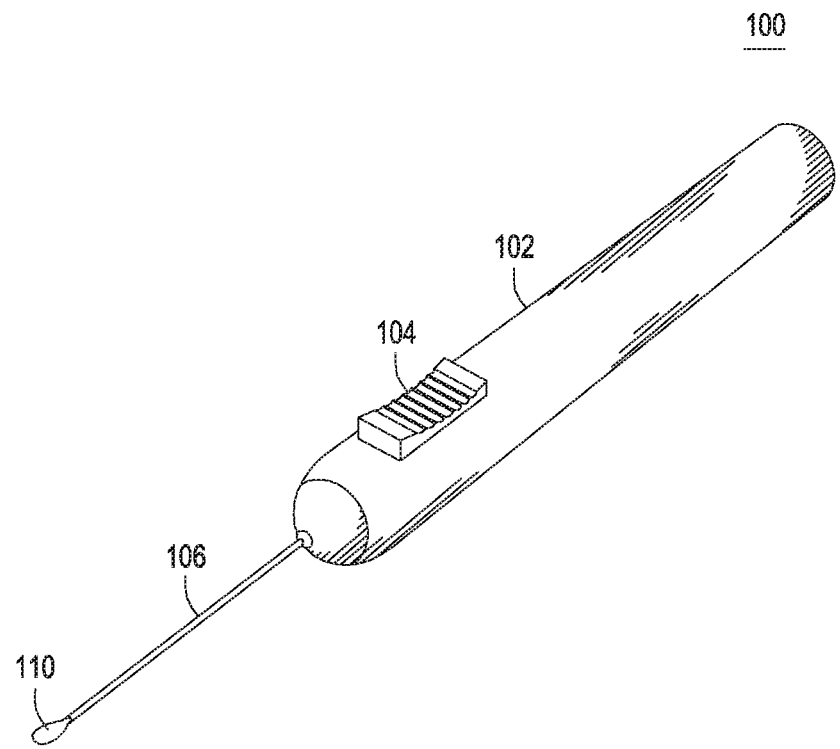
FIG. 1A is a perspective view of an extendable-retractable mirror device according to one embodiment.

Those skilled in the art will appreciate that FIGS. 1-8 are not necessarily to scale, and that several of the features may be exaggerated to more clearly illustrate various features. Those skilled in the art will also appreciate that the illustrated structures are only exemplary, and not limiting.

DETAILED DESCRIPTION

Before the present extendable-retractable mirror devices are described, it is to be understood that this disclosure is not limited to the specific embodiments described, as such may, of course, vary. It is also to be understood that the terminology used herein is for the purpose of describing particular aspects only and is not intended to limit the scope of the present disclosure.

Note that as used in the present specification and in the appended claims, the singular forms "a," "an," and "the" include plural referents unless the context clearly dictates otherwise.

Unless defined otherwise, all technical and scientific terms used herein have the same meaning as commonly understood by one of ordinary skill in the art to which this disclosure belongs. All publications mentioned herein are incorporated herein by reference for the purpose of describing and disclosing devices and methodologies that are described in the reference and which might be used in connection with this disclosure.

Where a range of values is provided, it is understood that each intervening value between the upper and lower limit of that range and any other stated or intervening value in that stated range is included as an embodiment of the disclosure. The upper and lower limits of these smaller ranges are also included as an embodiment of the disclosure, subject to any specifically excluded limit in the stated range. Where the stated range includes both the upper and lower limits, ranges excluding either of those included limits are also included as an embodiment of the disclosure.

In the following description, numerous specific details are set forth to provide a more thorough understanding of the present disclosure. However, it will be apparent to one of skill in the art upon reading the specification that the present disclosure may be practiced without one or more of these specific details. In other instances, features and procedures well-known to those skilled in the art have not been described in order to avoid obscuring the disclosure.

The present disclosure provides a small gauge extendable-retractable mirror device that can be delivered to the eye via a small incision (e.g., approximately 2.0 mm or less) for use in intraocular surgery. Other incision sizes are also possible. The mirror of the present disclosure can be used in, e.g., intraocular refractive and vitreoretinal surgery—or for diagnosis of conditions of the eye—to enable visualization of areas of the eye currently difficult or impossible to view, such as, e.g., behind the iris or in the angle of the eye. That is, the mirror of the present disclosure provides a surgeon an enhanced view of the surgical field. The surgical field may include any anatomy of a patient's eye, including the anterior segment, posterior segment, cornea, lens, vitreous chamber, blood vessels, retina, optic disc, and/or other biological tissue. The extendable-retractable mirror of the disclosure may be comprised of a very thin piece (e.g., approximately 0.001 inches) of a superelastic material that is coupled to an actuation rod and is initially located within a lumen of a small gauge cannula in a compact configuration (e.g., in a "rolled up" or "folded" configuration). Other compact configurations are also possible. The mirror may be manually (or, in some embodiments, automatically) extended from the cannula by the surgeon using, e.g., a sliding mechanism that slides the actuation rod forward within the cannula, deploying the mirror from the distal end (opposite the body of the device and toward the eye) of the cannula. In some embodiments, the surgeon may activate the sliding mechanism indirectly (e.g., through pressing a switch/button on the device to activate a motor coupled to the sliding mechanism or actuation rod for advancing/retracting the mirror from the distal end). In some embodiments, the mirror may be extended from the cannula via a button, toggle, wheel, or other actuatable component. As the mirror is deployed, the mirror may unroll or unfold into a flat/expanded configuration. Once the surgeon finishes using the mirror, the mirror may be retracted back into the cannula by sliding the actuation rod backward into the cannula (either manually or automatically). The mirror may be designed to automatically and correctly roll up or fold back into the cannula upon retraction.

FIG. 1A is a perspective view of an extendable-retractable mirror device 100 according to one embodiment. The extendable-retractable mirror device 100 as shown comprises a body 102 that houses a control slide 104 that slidably moves an actuation rod through a cannula 106 to deploy or extend mirror 110 distal from the device and into the eye. Once the mirror 110 has been deployed and used, the control slide 104 slidably retracts the actuation rod and the mirror 110 back into the cannula 106. The mirror is designed to automatically and correctly roll up/fold up into the cannula, as described below. In some embodiments, the body 102 may be made of a material that is easily sterilizable, such as plastic or metal. In some embodiments, the body 102 may not enter the eye when the mirror is deployed in the eye. In some embodiments, the portion of the extendable-retractable mirror device 100 that is sheathed in the cannula 106 (and possibly portions of the cannula 106) enter the eye. The cannula 106 may have a small gauge diameter, for example approximately in a range of 16-30 gauge. In a more specific example, the cannula 106 diameter may be approximately in a range of 20-27 gauge. Other gauges are also possible. The internal diameter of cannula 106 may be between approximately 400 microns and approximately 600 microns, between approximately 400 microns and approximately 550 microns, between approximately 400 microns and approximately 500 microns, and/or other suitable size. The length of cannula 106 may be between approximately 20 mm and approximately 50 mm, between approximately 20 mm and approximately 40 mm, and/or other suitable size. Cannula 106 can have a cross-section shaped as a polygon, an ellipse, or other suitable shape, and in some embodiments cannula 106 has a circular cross-section. The cannula 106 may be made of metal (e.g., stainless steel or titanium), medical grade tubing or plastic or other suitable polymer. Other materials are also contemplated.

In some embodiments, the mirror 110 may be fabricated from a very thin piece of material and/or be superelastic. For example, the mirror 110 may have a thickness in a range of approximately 0.0003 inches to 0.012 inches, in a range of approximately 0.0004 inches to 0.011 inches, in a range of approximately 0.0005 inches to 0.010 inches, in a range of approximately 0.0006 inches to 0.009 inches, in a range of approximately 0.0007 inches to 0.008 inches, or in a range of approximately 0.0008 inches to 0.0010 inches. Other thickness ranges are also possible. In some embodiments, the mirror 110 may be made of nitinol. Nitinol is an alloy of titanium and nickel, where each element in the nitinol alloy may be present in roughly equal atomic percentages. Nitinol alloys may include those that exhibit superelasticity at room/body temperature. Nitinol alloys exhibit two closely related and unique properties: shape memory and superelasticity. Shape memory is the ability of nitinol to undergo deformation at one temperature, then recover its original, undeformed shape upon heating above its transformation temperature. Superelasticity occurs at a narrow temperature range just above the transformation temperature; in this case, no heating may be necessary to cause the undeformed shape to recover, and the material exhibits enormous elasticity; e.g., approximately 10-30 times that of ordinary metal. In some embodiments, nitinol alloys may form the body of the mirror 110. Other nitinol configurations are also possible to allow the mirror to collapse into the cannula 106 and open into an expanded configuration when deployed out of the cannula 106.

In some embodiments, the mirror 110 may be polished to provide a reflective mirror surface. Other reflective surface types are also contemplated. For example, a thin mirrored film, such as a coat of metal or a metalized plastic film, may be applied to at least one side of the mirror 110. As an example, silver (which may improve reflectivity and reduce image distortion) or rhodium (which may be more durable) may be coated over the surface of the mirror. In some embodiments, the reflective materials (such as a reflective silver foil) may be placed over a nitinol coil. In some embodiments, the mirror 110 may be laser cut from a sheet of material (such as nitinol) or, e.g., mechanical cutting methods can be used to form the mirror 110.

In some embodiments, the mirror 110 may be superelastic (which term is intended herein as a synonym for the somewhat more technically precise term "pseudoelastic"). A superelastic mirror 110 may be able to withstand a significant amount of deformation when a load is applied and return to its original shape when the load is removed. (Those skilled in the art will appreciate that this property is distinct from, although related to, "shape memory", which refers to a property exhibited by some materials in which an object that is deformed while below the material's transformation temperature returns to its former shape when warmed to above the transformation temperature. Nitinol exhibits both properties; superelasticity is exhibited above the transformation temperature.) Of course, those skilled in the art will appreciate that other materials that are superelastic may be used instead of nitinol in some embodiments.

Figure 1B:
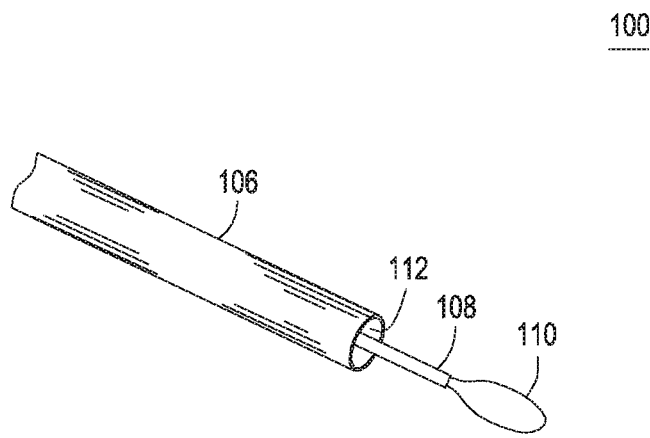
FIG. 1B is a perspective view of the distal portion of an extendable-retractable mirror device according to an embodiment.

FIG. 1B is a perspective view of the distal end of an extendable-retractable mirror device according to an embodiment. The distal end of the extendable-retractable mirror device comprises a cannula 106 and an actuation rod 108 that is slidably disposed inside the lumen of cannula 106 (the distal lumen 112 of cannula 106 is shown). The actuation rod 108 may be coupled to mirror 110 at the distal end of the actuation rod 108. In some embodiments, the actuation rod 108 deploys mirror 110 distal from the body of the extendable-retractable mirror device and into the eye. Once the mirror 110 has been deployed and used, the actuation rod 108 slidably retracts into the cannula 106, retracting the mirror 110. The embodiment shown in FIG. 1B depicts an actuation rod 108 that can extend a distance from the distal lumen 112 of the cannula 106. The actuation rod 108 may be made of metal (e.g., stainless steel or titanium) or plastic (other materials are also possible). In some embodiments, actuation rod 108 may be flexible.

Figure 2:
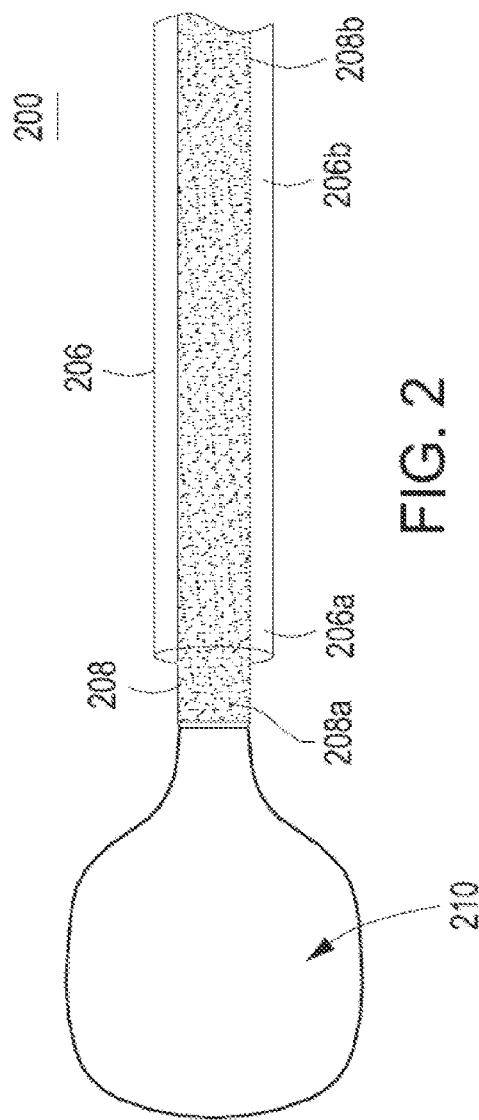
FIG. 2 is a top view of the distal portion of an extendable-retractable mirror device in an extended configuration, according to one embodiment.

FIG. 2 is a top view of the distal portion 200 of an extendable-retractable mirror device according to an embodiment. FIG. 2 shows cannula 206 (shown as transparent in this figure), actuation rod 208 slidably disposed within cannula 206, and a mirror 210 coupled to the distal end of actuation rod 208. The distal end of cannula 206 is shown at 206a, and the proximal end of cannula 206 (e.g., the end of the cannula 206 toward the body of the device) is shown at 206b. Likewise, the distal end of actuation rod 208 is shown at 208a, and the proximal end of actuation rod 208 (e.g., the end of the actuation rod 208 toward the body of the device) is shown at 208b.

Figure 3:
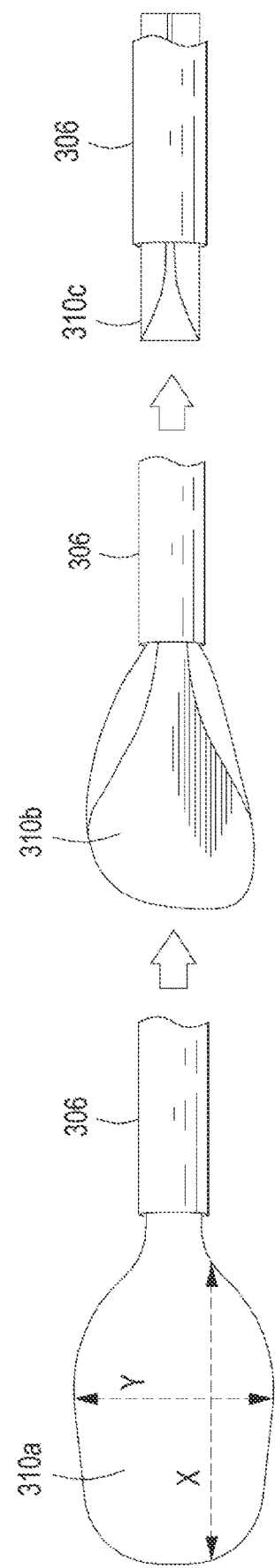
FIG. 3 is a perspective view of the distal portion of an extendable-retractable mirror device showing the extendable-retractable mirror being retracted.

FIG. 3 is a series of perspective views of the distal portion 300 of an extendable-retractable mirror device according to an embodiment showing the extendable-retractable mirror being retracted. FIG. 3 shows cannula 306—which is shown with the proximal end cut away—through which the actuation rod is slidably disposed and able to deploy (extend) and retract the mirror. FIG. 3 shows three stages of extension and retraction. When mirror 310a is fully extended, the mirror 310a may have an x dimension in a range of approximately 1.2-6.5 mm. In a more specific example, the mirror may have an x dimension in a range of approximately 2.0-5.5 mm (or, more specifically, in a range of approximately 2.5-5.0 mm). The mirror 310a may have a y dimension in a range of approximately 1.2-6.5 mm. In a more specific example, the mirror 310a may have a y dimension in a range of approximately 2.0-5.5 mm (or, more specifically, in a range of approximately 2.5-5.0 mm). Other mirror sizes are also contemplated based on, for example, surgeon preference, surgery type (e.g., cataract removal, vitrectomy, etc.) and anatomy to be viewed. For example, a mirror with dimensions smaller than the diameter of the lens capsule of the human eye may be used during cataract removal to view different areas of lens capsule. As another example, a mirror with dimensions smaller than the height and width of the vitreous chamber of the eye may be used to view different areas of the interior of the vitreous chamber and/or posterior of the eye. Many adult human eyes have a diameter in a range of approximately 19-35 mm. (Other dimensions are also possible. For example, pediatric eye dimensions may be substantially smaller.) Mirror dimensions for use in adult eyes may thus be less than 35 mm (and, in some embodiments, may be substantially smaller as provided in several examples above).

Figure 7:
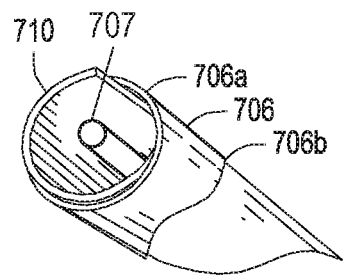
FIG. 7 is an end view of the distal portion of an extendable-retractable mirror device showing the extendable-retractable mirror retracted into the cannula along with an illumination source.

In addition to viewing different parts of the eye, the mirror may further be used to bounce/direct energy (e.g., laser light) onto different parts of the eye. For example, an ophthalmic laser (e.g., positioned inside or outside the eye) may direct laser light that is bounced off the surface of the mirror to reflect the laser light toward an anatomical structure in the eye (e.g., that is not co-linear with the laser output). As another example, a light source (such as nanofiber 707 shown in FIG. 7) may direct light off of the surface of the mirror to illuminate a portion of the eye. The nanofiber 707 may be coaxial to the cannula 706 and may be attached to an internal component of the cannula 706 (e.g. attached to actuation rod 108 in the cannula 706 to be held in a coaxial configuration as shown in FIG. 7). Other configurations are also contemplated (e.g., the nanofiber may be attached to an internal or external sidewall of the cannula 706). While shown inside the eye in FIG. 7, in some embodiments, the light source may be outside the eye. The light source (e.g., nanofiber 707) may provide different levels of illumination (e.g., controllable at the console or, for example, through a switch on the body 102). In some embodiments, the light source may also provide different light colors (e.g., selectable by the user through the console or, for example, through a switch on the body 102).

FIG. 3 further shows the mirror 310b in the process of being retracted into cannula 306 via the actuation rod. Further, mirror 310c is shown almost entirely retracted into cannula 306 via the actuation rod.

Figure 4:
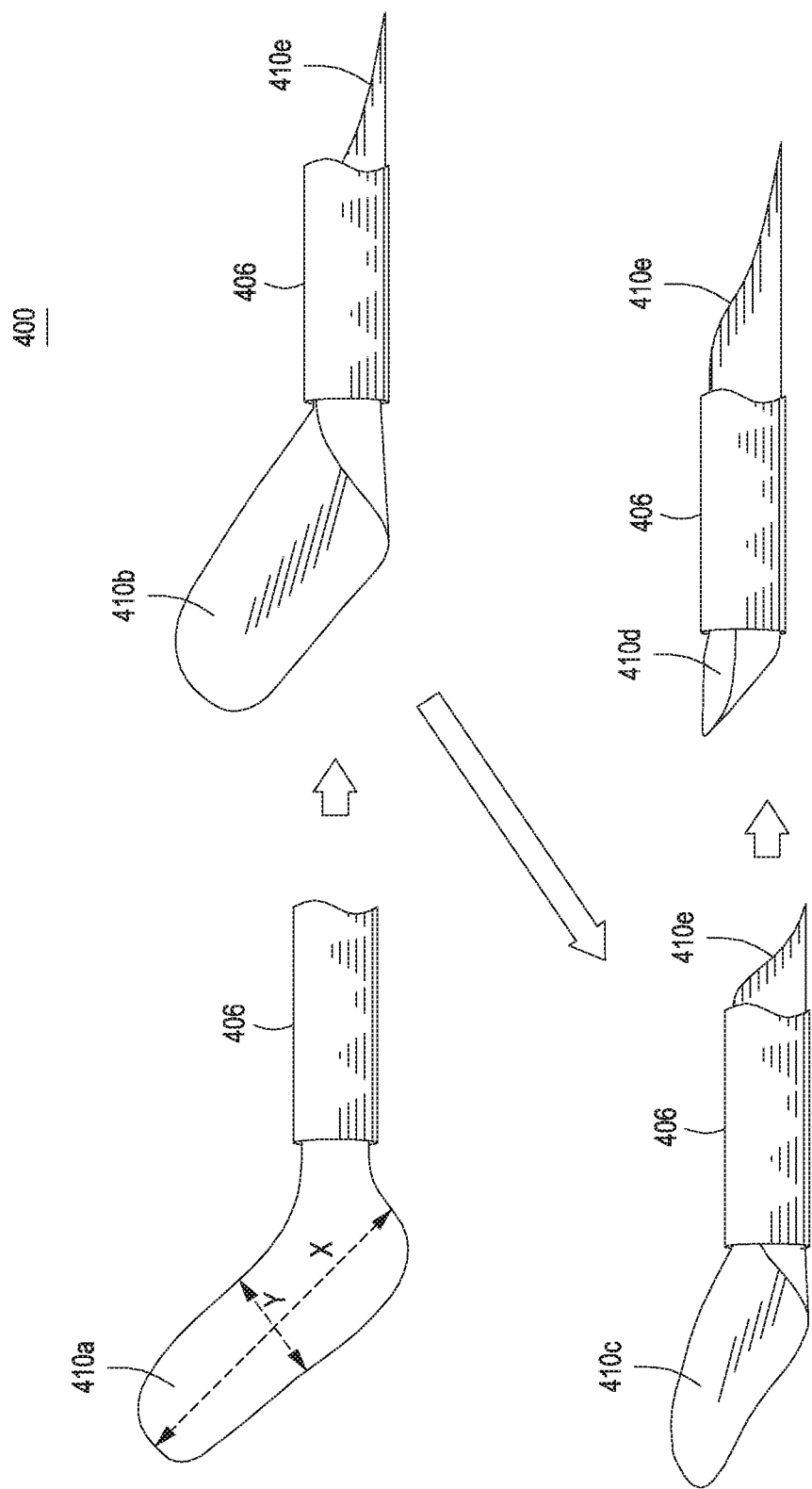
FIG. 4 is a perspective view of the distal portion of an alternative embodiment of the extendable-retractable mirror device showing the extendable-retractable mirror being retracted.

FIG. 4 is a series of perspective views of the distal portion 400 of an extendable-retractable mirror device according to another embodiment showing the extendable-retractable mirror being retracted. FIG. 4 shows cannula 406—which is shown with the proximal end cut away—through which the actuation rod is slidably disposed and able to deploy (extend) and retract the mirror (shown in four stages of extension and retraction). As discussed above, the mirror may have various dimensions based on, for example, surgeon preference, surgery type (e.g., cataract removal, vitrectomy, etc.) and anatomy to be viewed. In some embodiments, when mirror 410a is fully extended, the mirror 410a may have an x dimension in a range of approximately 1.2-6.5 mm. In a more specific example, the mirror 410a may have an x dimension in a range of approximately 2.0-5.5 mm (or, more specifically, in a range of approximately 2.5-5.0 mm). Mirror 410a may have a y dimension in a range of approximately 1.2-5.5 mm. In a more specific example, the mirror 410a may have a y dimension in a range of approximately 2.0-4.5 mm (or, more specifically, in a range of approximately 2.5-3.5 mm). Mirror 410b is shown in the process of being retracted into cannula 406 via the actuation rod, where the proximal end (410e) of the mirror is shown from the cut away proximal end of the cannula 406. The cannula is cut away in this panel to demonstrate the folding/rolling of the mirror. Mirror 410c is further in the process of being retracted into cannula 406 via the actuation rod, where more of the rolled up/folded up proximal end 410e of the mirror is shown. Finally, the last panel shows mirror 410d almost entirely retracted into cannula 406 via the actuation rod.

Figure 5:
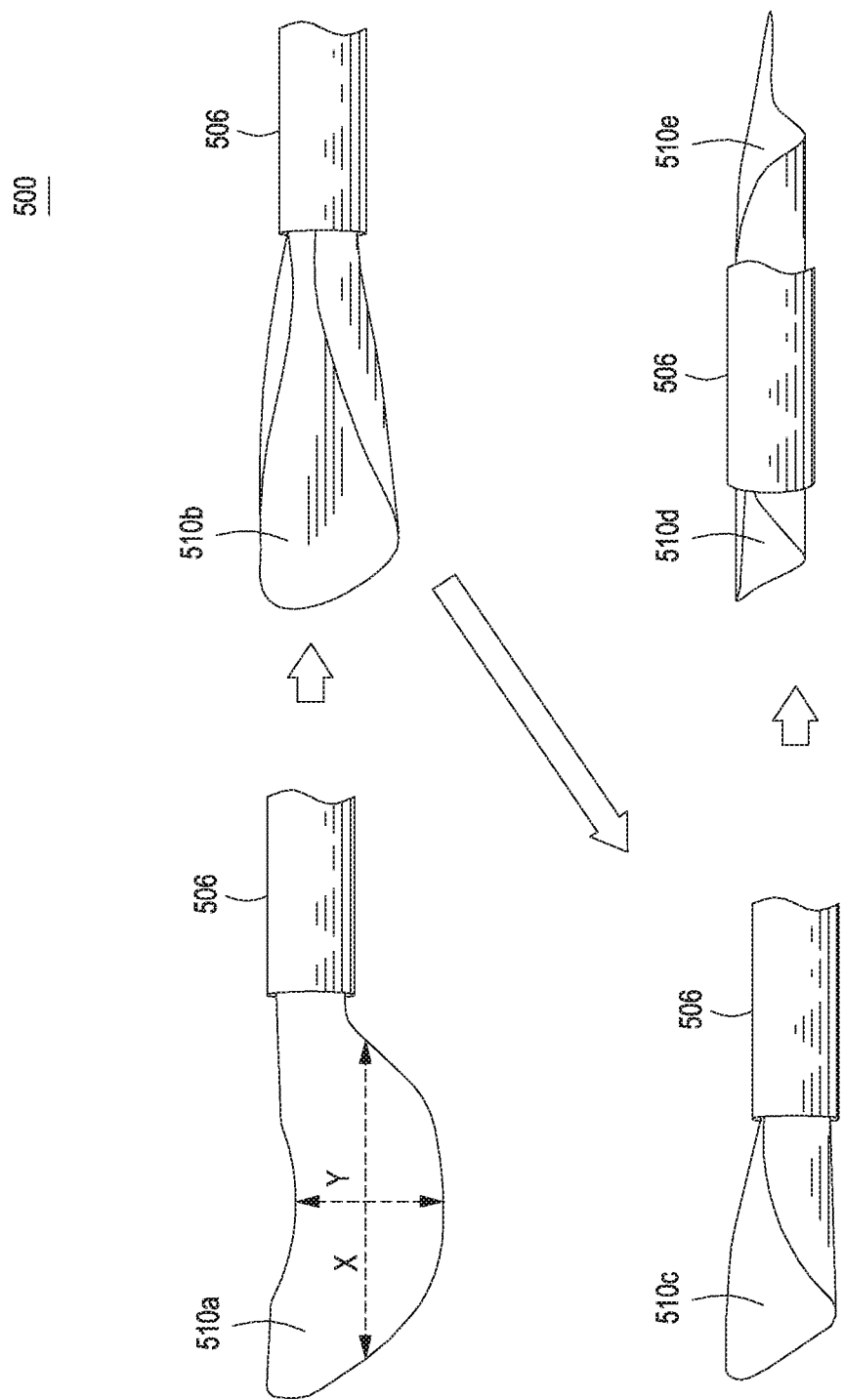
FIG. 5 is a perspective view of the distal portion of an extendable-retractable mirror device according to yet another alternative embodiment showing the extendable-retractable mirror being retracted.

FIG. 5 is a series of perspective views of the distal portion 500 of an extendable-retractable mirror device according to another embodiment showing the extendable-retractable mirror being retracted. FIG. 5 shows cannula 506—which is shown with the proximal end cut away—through which the actuation rod is slidably disposed and able to deploy (extend) and retract the mirror (shown in four stages of extension and retraction). Again, mirror 510a may have various dimensions as discussed above. In some embodiments, when mirror 510a is fully extended, mirror 510a may have an x dimension in a range of approximately 1.2-6.5 mm. In a more specific example, mirror 510a may have an x dimension in a range of approximately 2.0-5.5 mm (or, more specifically, or in a range of approximately 2.5-5.0 mm). When mirror 510a is fully extended, mirror 510a may have a y dimension in a range of approximately 1.2-5.5 mm. In a more specific example, mirror 510a may have a y dimension in a range of approximately 2.0-4.5 mm (or, more specifically, in a range of approximately 2.5-3.5 mm). Mirror 510b is shown in the process of being retracted into cannula 506 via the actuation rod. Mirror 510c is further in the process of being retracted into cannula 506 via the actuation rod. Finally, mirror 510d is almost entirely retracted into cannula 506 via the actuation rod, where more of the proximal end (510e) of the mirror is shown. The cannula is cut away to demonstrate the proximal end of the mirror in the rolled/folded configuration.

Figure 6:
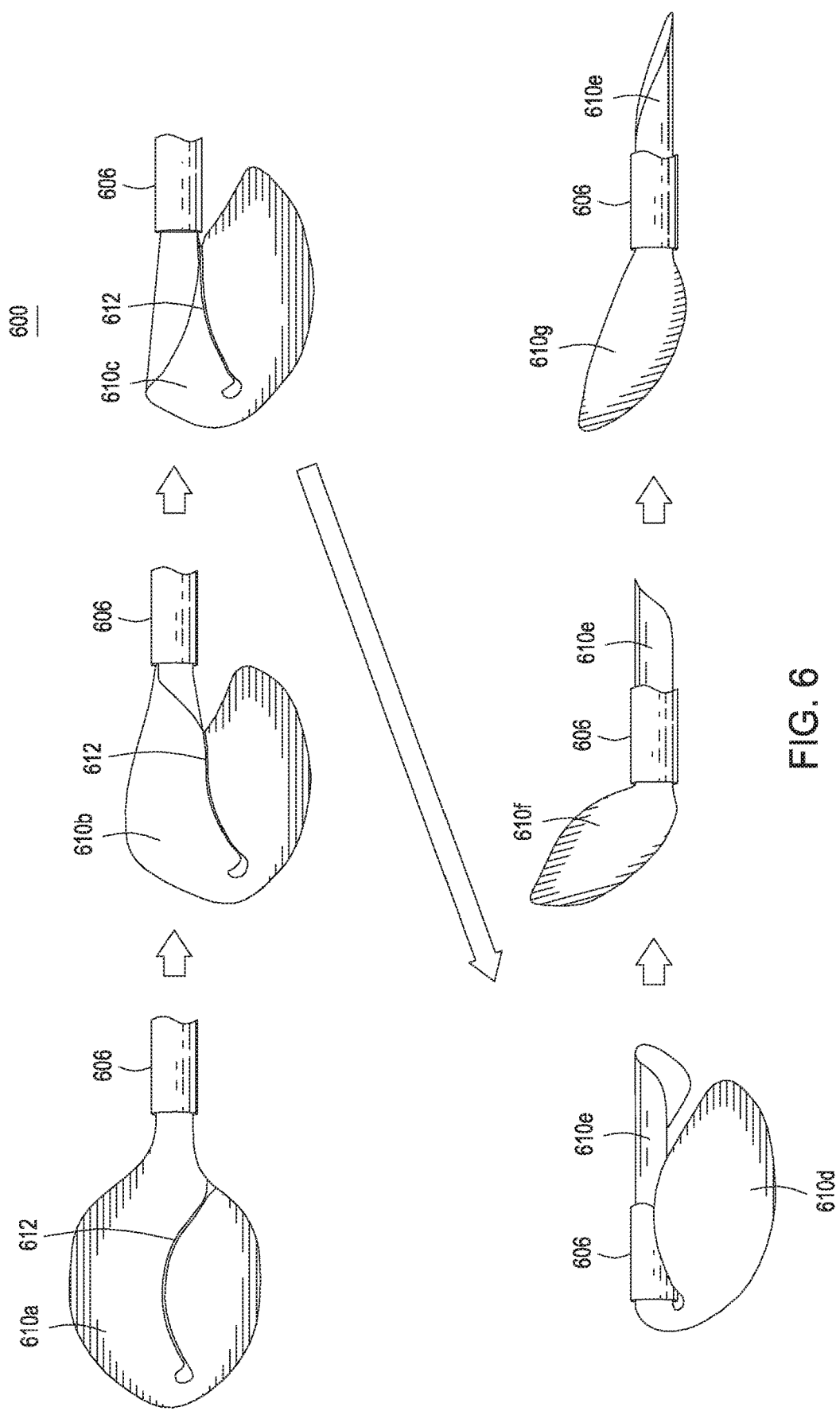
FIG. 6 is a perspective view of the distal portion of an extendable-retractable mirror device according to yet another alternative embodiment showing the extendable-retractable mirror being retracted.

FIG. 6 is a series of perspective views of the distal portion 600 of an extendable-retractable mirror device according to another embodiment showing the extendable-retractable mirror being retracted. FIG. 6 shows cannula 606, through which the actuation rod is slidably disposed and able to deploy (extend) and retract the mirror (shown in six stages of extension and retraction). In some embodiments, the mirror may include one or more slits 612 to allow one to configure a mirror with a large area that is still able to fold into the cannula. As noted above, various dimensions for the mirror are possible. As one example, when mirror 610a is fully extended, mirror 610a may have an x dimension in a range of approximately 1.2-6.5 mm. In a more specific example, mirror 610a may have an x dimension in a range of approximately 2.0-5.5 mm (or, more specifically, in a range of approximately 2.5-5.0 mm). When mirror 610a is fully extended, mirror 610a may have a y dimension in a range of approximately 1.2-6.5 mm. In a more specific example, mirror 610a may have a y dimension in a range of approximately 2.0-5.5 mm (or, more specifically, in a range of approximately 2.5-5.0 mm). Mirror 610b is in the process of being retracted into cannula 606 via the actuation rod. Mirror 610c is further in the process of being retracted into cannula 506 via the actuation rod, and mirrors 610d and 610f are even further into the process of being retracted into the cannula. Finally, mirror 610g is almost entirely retracted into cannula 606. The proximal ends 610e of the retracted mirror are shown. The cannula is shown cut away to demonstrate the proximal end of the mirror in its rolled/folded configuration. Note that the embodiments of the mirror exemplified herein have differing configurations such as in FIGS. 3 and 6 where the x dimension and y dimension of the mirror are substantially the same; or the configurations such as in FIGS. 4 and 5 where the x dimension of the mirror is greater than the y dimension of the mirror. Any suitable mirror shape may be used, including square, round, polygonal, irregular, or other configurations. In some configurations, the mirror may have a planar surface. In other configurations, the mirror may have a convex or concave surface (e.g., to add magnification (concave) and/or view a wider area/angle (convex) versus a planar surface). In some embodiments, one side of the mirror may be concave while the other side of the mirror is convex to provide different viewing abilities depending on which side of the mirror is being viewed. Other magnification configurations are also contemplated (e.g., different etch patterns on the surface or different materials used to coat the mirror or as the mirror material itself).

FIG. 7 is an end view of the distal portion 700 of the extendable-retractable mirror device with the extendable-retractable mirror retracted into the cannula. FIG. 7 shows the end of cannula 706, with mirror 710 rolled up and disposed within cannula 706. In some embodiments, the mirror may be further retracted into the cannula (such that no portion of the mirror is protruding out of the cannula 706). In some embodiments, the mirror device further includes an integrated nanofiber 707 to provide illumination to the mirror 710. An end of the nanofiber 707 that emits light is shown in FIG. 7. In some embodiments, the nanofiber 707 may run along the interior of the cannula 706. In some embodiments, the integrated nanofiber 707 is coaxial to the actuation rod. In some embodiments, the nanofiber 707 may be surrounded on its exterior by a tubular support made of a rigid material (e.g., rigid plastic or metal) to hold the nanofiber 707 in place coaxial to the cannula 706. The tubular support may be attached to an interior of the cannula 706 (e.g, attached to actuation rod 108 inside the cannula 706). In some embodiments, the nanofiber 707 may be stiff enough to be held in place without a tubular support. The mirror 710 may collapse in the area around the nanofiber 707 as it is withdrawn into the cannula 706. Other embodiments for the nanofiber 707 are also contemplated (e.g., the nanofiber may be attached to the outside surface of the cannula 706).

Figure 8:
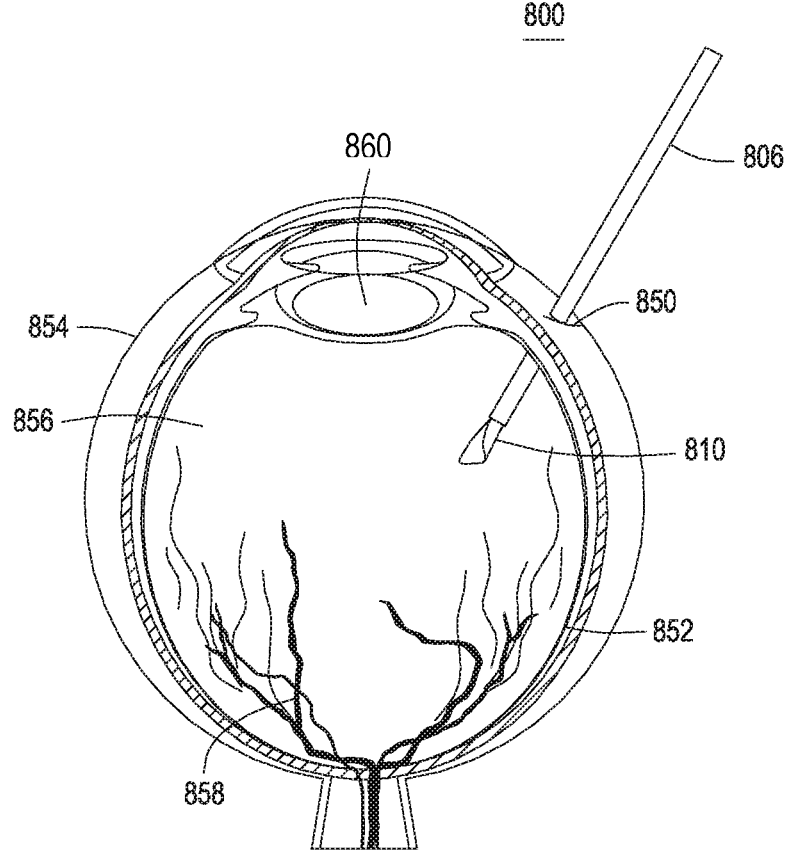
FIG. 8 is a cross-sectional side view of an eye with the distal portion of an extendable-retractable mirror device inserted into the eye.

FIG. 8 is a cross-sectional side view of an eye 800 with the distal portion of an extendable-retractable mirror device inserted into an eye. The distal portion of the extendable-retractable mirror device is seen, including cannula 806 and mirror 810. Also seen is incision 850, through which cannula 806 is inserted, retina 852, conjunctiva/sclera 854, vitreous body 856, lens 860, and retinal blood vessels 858.

The preceding merely illustrates the principles of the disclosure. It will be appreciated that those skilled in the art will be able to devise various arrangements which, although not explicitly described or shown herein, embody the principles of the disclosure and are included within its spirit and scope. Furthermore, all examples and conditional language recited herein are principally intended to aid the reader in understanding the principles of the disclosure and the concepts contributed by the inventors to furthering the art, and are to be construed as being without limitation to such specifically recited examples and conditions. Moreover, all statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the appended claims. In the claims that follow, unless the term "means" is used, none of the features or elements recited therein should be construed as means-plus-function limitations pursuant to 35 U.S.C. § 112, ¶6.

The invention claimed is:

1. A small gauge extendable-retractable mirror, comprising:
    a handheld body having a proximal end and a distal end,
    a cannula having a proximal end and a distal end, wherein the proximal end of the cannula is coupled to and extending from the distal end of the body, the cannula defining an internal actuation rod passageway;
    an actuation rod slidably disposed within the actuation rod passageway;
    an actuator coupled to the body, wherein the actuation rod extends and retracts the actuation rod;
    a mirror coupled to the actuation rod, wherein the mirror retracts and extends from the distal end of the cannula;
    wherein when retracted into the cannula, the mirror has a compact configuration that can be withdrawn through a 2 mm (millimeter) incision, and when extended from the cannula, the mirror has an expanded configuration with a viewing surface having an x and y dimension that are each larger than 2 millimeters.

2. The small gauge extendable-retractable mirror of claim 1, wherein, in the expanded configuration, the mirror has a reflective surface that has an x dimension approximately in a range of 1.2-6.5 mm.

3. The small gauge extendable-retractable mirror of claim 1, wherein, in the expanded configuration, the mirror has a reflective surface that has a y dimension approximately in a range of 1.2-6.5 mm.

4. The small gauge extendable-retractable mirror of claim 1, wherein, in the expanded configuration, the mirror has an x dimension of 2.5-5.0 mm and a y dimension of 2.5-5.0 mm.

5. The small gauge extendable-retractable mirror of claim 1, wherein the mirror comprises one or more slits.

6. The small gauge extendable-retractable mirror of claim 1, wherein the mirror is made of nitinol.

7. The small gauge extendable-retractable mirror of claim 6, wherein a first opposing surface of the nitinol mirror is the reflective surface that is formed by polishing the first opposing surface of the extendable-retractable mirror.

8. The small gauge extendable-retractable mirror of claim 1, wherein a first opposing surface of the mirror is the reflective surface that is formed by deposing a thin layer of reflective material on the first opposing surface of the mirror.

9. The small gauge extendable-retractable mirror of claim 8, wherein the reflective material is metalized plastic film.

10. The small gauge extendable-retractable mirror of claim 1, wherein both opposing surfaces of the mirror are reflective.

11. The small gauge extendable-retractable mirror of claim 1, further comprising a switch actuator, coupled to the body, that extends and retracts the actuation rod.

12. The small gauge extendable-retractable mirror of claim 1, further comprising an integrated nanofiber to provide illumination to the mirror.

13. The small gauge extendable-retractable mirror of claim 12, wherein the integrated nanofiber is coaxial to the actuation rod.

14. The small gauge extendable-retractable mirror of claim 1, wherein the opposing surfaces of the mirror are flat.

15. The small gauge extendable-retractable mirror of claim 1, wherein the opposing surfaces of the mirror are curved.

16. The small gauge extendable-retractable mirror of claim 1, wherein the mirror is fully deployed from the distal end of the cannula.

17. The small gauge extendable-retractable mirror of claim 1, wherein the mirror is fully retracted into the cannula.

* * * * *